United States Patent
Michelson

(10) Patent No.: US 7,452,359 B1
(45) Date of Patent: Nov. 18, 2008

(54) APPARATUS FOR INSERTING SPINAL IMPLANTS

(75) Inventor: Gary Karlin Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 08/480,684

(22) Filed: Jun. 7, 1995

Related U.S. Application Data

(60) Division of application No. 07/968,240, filed on Oct. 29, 1992, now Pat. No. 5,741,253, which is a continuation of application No. 07/698,674, filed on May 10, 1991, now abandoned, which is a division of application No. 07/205,935, filed on Jun. 13, 1988, now Pat. No. 5,015,247.

(51) Int. Cl.
*A61F 17/56* (2006.01)
(52) U.S. Cl. .......................... 606/60; 606/61
(58) Field of Classification Search .................. 606/60, 606/61, 72–79, 80–81; 623/16.1, 17.1
See application file for complete search history.

(56) References Cited

U.S. PATENT DOCUMENTS

| | | | |
|---|---|---|---|
| 350,420 A | 10/1886 | Dillon | |
| 1,137,585 A | 4/1915 | Craig | |
| 2,065,659 A | 12/1936 | Cullen | |
| 2,100,319 A | 11/1937 | Brown et al. | |
| 2,181,746 A | 11/1939 | Siebrandt | |
| 2,243,718 A | 5/1941 | Moreira | |
| 2,372,622 A | 3/1945 | Fassio | |
| 2,514,665 A | 7/1950 | Myller | |
| 2,537,070 A | 1/1951 | Longfellow | |
| 2,543,780 A | 3/1951 | Hipps et al. | |
| 2,677,369 A | 5/1954 | Knowles | |
| 2,774,350 A | 12/1956 | Cleveland | |
| 2,789,558 A | 4/1957 | Rush | |
| 2,832,343 A | 4/1958 | Mose | |
| 2,842,131 A | 7/1958 | Smith | |
| 2,878,809 A | 3/1959 | Treace | |
| 2,984,241 A | 5/1961 | Carlson | |
| 3,128,768 A | 4/1964 | Geistauts | |
| 3,298,372 A | 1/1967 | Peinberg | |
| 3,426,364 A | 2/1969 | Lumb | |
| 3,486,505 A | 12/1969 | Morrison | |
| 3,604,487 A | 9/1971 | Gilbert | |
| 3,605,123 A | 9/1971 | Hahn | |

(Continued)

FOREIGN PATENT DOCUMENTS

DE     1 961 531     7/1970

(Continued)

OTHER PUBLICATIONS

Cloward, Ralph B.; Surgical Techniques for Lumbar Disc Lesions; Codman; Signature Serial 3.

(Continued)

*Primary Examiner*—Michael A. Brown
(74) *Attorney, Agent, or Firm*—Martin & Ferraro, LLP

(57) ABSTRACT

An artificial spinal implant is disclosed which when placed between two adjacent vertebrae directly participates and is incorporated in the ensuing fusion. Instrumentation and procedure is also disclosed.

134 Claims, 6 Drawing Sheets

U.S. PATENT DOCUMENTS

| | | | |
|---|---|---|---|
| 3,618,611 A | 11/1971 | Urban | |
| 3,661,291 A | 5/1972 | Hetzer | |
| 3,709,219 A | 1/1973 | Halloran | |
| 3,719,186 A | 3/1973 | Merig, Jr. | |
| 3,720,959 A | 3/1973 | Hahn | |
| 3,750,652 A | 8/1973 | Sherwin | |
| 3,799,229 A | 3/1974 | Johnson | |
| 3,834,393 A | 9/1974 | Goggins | |
| 3,848,601 A * | 11/1974 | Ma | 623/17 |
| 3,855,638 A | 12/1974 | Pilliar | |
| 3,867,728 A | 2/1975 | Stubstad et al. | |
| 3,867,950 A | 2/1975 | Fischell | |
| 3,875,595 A * | 4/1975 | Froning | 623/17 |
| 3,888,260 A | 6/1975 | Fischell | |
| 3,892,232 A | 7/1975 | Neufeld | |
| 3,905,047 A | 9/1975 | Long | |
| 3,915,151 A | 10/1975 | Kraus | |
| 3,916,907 A | 11/1975 | Peterson | |
| 3,918,440 A | 11/1975 | Kraus | |
| 3,942,535 A | 3/1976 | Schulman | |
| 3,948,262 A | 4/1976 | Zaffaroni | |
| 3,952,334 A | 4/1976 | Bokros et al. | |
| 3,955,280 A | 5/1976 | Sneer | |
| 3,979,828 A | 9/1976 | Taylor | |
| 3,987,499 A | 10/1976 | Scharbach et al. | |
| 4,010,737 A | 3/1977 | Vilaghy et al. | |
| 4,016,651 A | 4/1977 | Kawahara et al. | |
| 4,027,392 A | 6/1977 | Sawyer et al. | |
| D245,259 S | 8/1977 | Shen | |
| 4,051,905 A | 10/1977 | Kleine | |
| 4,059,115 A | 11/1977 | Jumashev et al. | |
| 4,067,340 A | 1/1978 | LeNoir | |
| 4,070,514 A | 1/1978 | Entherly et al. | |
| 4,082,097 A | 4/1978 | Mann et al. | |
| 4,086,701 A | 5/1978 | Kawahara et al. | |
| 4,124,026 A | 11/1978 | Berner et al. | |
| 4,142,517 A | 3/1979 | Stravropoulos et al. | |
| 4,153,053 A | 5/1979 | Figallo | |
| 4,168,326 A | 9/1979 | Broemer et al. | |
| 4,175,555 A | 11/1979 | Herbert | |
| 4,177,524 A | 12/1979 | Grell et al. | |
| 4,181,457 A | 1/1980 | Holmes | |
| 4,185,383 A | 1/1980 | Heimke et al. | |
| 4,186,486 A | 2/1980 | Gordon | |
| 4,197,850 A | 4/1980 | Schulman et al. | |
| 4,206,516 A | 6/1980 | Pilliar | |
| 4,222,128 A | 9/1980 | Tomonaga et al. | |
| D257,511 S | 11/1980 | Zahn | |
| 4,232,679 A | 11/1980 | Schulman | |
| 4,237,948 A | 12/1980 | Jones et al. | |
| 4,258,716 A | 3/1981 | Sutherland | |
| 4,259,072 A | 3/1981 | Hirabayashi et al. | |
| 4,262,369 A | 4/1981 | Roux | |
| 4,271,832 A | 6/1981 | Evans et al. | |
| D260,525 S | 9/1981 | Lassiter | |
| 4,289,123 A | 9/1981 | Dunn | |
| 4,293,962 A | 10/1981 | Fuson | |
| 4,309,777 A | 1/1982 | Patil | |
| 4,313,434 A | 2/1982 | Segal | |
| 4,315,340 A | 2/1982 | Veldman | |
| 4,328,593 A | 5/1982 | Sutter et al. | |
| 4,332,036 A | 6/1982 | Sutter et al. | |
| 4,333,469 A | 6/1982 | Jeffcoat et al. | |
| 4,337,773 A | 7/1982 | Raftopoulos et al. | |
| 4,341,206 A | 7/1982 | Perrett et al. | |
| 4,349,921 A | 9/1982 | Kuntz | |
| 4,356,572 A | 11/1982 | Guillemin et al. | |
| 4,356,828 A | 11/1982 | Jamshidi | |
| 4,373,217 A | 2/1983 | Draenert | |
| 4,401,112 A | 8/1983 | Rezaian | |
| 4,405,319 A | 9/1983 | Cosentino | |
| 4,414,979 A | 11/1983 | Hirshorn et al. | |
| 4,423,721 A | 1/1984 | Otte et al. | |
| 4,439,152 A | 3/1984 | Small | |
| 4,444,184 A | 4/1984 | Oretorp | |
| 4,450,834 A | 5/1984 | Fischer | |
| 4,466,429 A | 8/1984 | Loscher et al. | |
| 4,484,570 A | 11/1984 | Sutter et al. | |
| 4,488,549 A | 12/1984 | Lee et al. | |
| 4,492,226 A | 1/1985 | Belykh et al. | |
| 4,494,535 A | 1/1985 | Haig | |
| 4,497,320 A | 2/1985 | Nicholson et al. | |
| 4,501,269 A * | 2/1985 | Bagby | 128/92 G |
| 4,507,115 A | 3/1985 | Kambara et al. | |
| RE31,865 E | 4/1985 | Roux | |
| 4,522,201 A | 6/1985 | Tongue | |
| 4,530,360 A | 7/1985 | Duarte | |
| 4,535,374 A | 8/1985 | Anderson et al. | |
| 4,535,485 A | 8/1985 | Ashman et al. | |
| 4,542,539 A | 9/1985 | Rowe, Jr. et al. | |
| 4,545,374 A | 10/1985 | Jacobson | |
| 4,547,390 A | 10/1985 | Ashman et al. | |
| 4,549,547 A | 10/1985 | Brighton et al. | |
| 4,552,200 A | 11/1985 | Sinha et al. | |
| 4,553,273 A | 11/1985 | Wu | |
| 4,554,914 A | 11/1985 | Kapp et al. | |
| D281,814 S | 12/1985 | Pratt et al. | |
| 4,570,623 A | 2/1986 | Ellison et al. | |
| 4,570,624 A | 2/1986 | Wu | |
| 4,589,414 A | 5/1986 | Yoshida et al. | |
| 4,592,346 A | 6/1986 | Jurgutis | |
| 4,599,086 A | 7/1986 | Doty | |
| 4,600,000 A | 7/1986 | Edwards | |
| 4,602,638 A | 7/1986 | Adams | |
| 4,603,694 A | 8/1986 | Wheeler | |
| 4,604,995 A | 8/1986 | Stephens | |
| 4,608,052 A | 8/1986 | Van Kampen et al. | |
| 4,611,581 A | 9/1986 | Steffee | |
| 4,612,053 A | 9/1986 | Brown et al. | |
| 4,619,264 A | 10/1986 | Singh | |
| 4,627,434 A | 12/1986 | Murray | |
| 4,628,921 A | 12/1986 | Rousso | |
| 4,634,720 A | 1/1987 | Dorman et al. | |
| 4,636,217 A | 1/1987 | Ogilvie et al. | |
| 4,636,526 A | 1/1987 | Dorman et al. | |
| 4,645,503 A | 2/1987 | Lin et al. | |
| 4,653,486 A | 3/1987 | Coker | |
| 4,653,509 A | 3/1987 | Oloff et al. | |
| 4,655,777 A | 4/1987 | Dunn | |
| 4,657,550 A | 4/1987 | Daher | |
| 4,661,536 A | 4/1987 | Dorman et al. | |
| 4,664,567 A | 5/1987 | Edwards | |
| 4,665,920 A | 5/1987 | Campbell | |
| 4,677,883 A | 7/1987 | Lee | |
| 4,677,972 A | 7/1987 | Tornier | |
| 4,693,721 A | 9/1987 | Ducheyne | |
| 4,696,290 A | 9/1987 | Steffee | |
| 4,698,375 A | 10/1987 | Dorman et al. | |
| 4,710,075 A * | 12/1987 | Davison | 606/80 |
| 4,713,003 A | 12/1987 | Symington et al. | |
| 4,713,004 A | 12/1987 | Linkow et al. | |
| 4,713,006 A | 12/1987 | Hakamatsuka et al. | |
| 4,714,469 A | 12/1987 | Kenna | |
| 4,721,103 A | 1/1988 | Freedland | |
| 4,733,657 A | 3/1988 | Kluger | |
| 4,736,738 A | 4/1988 | Lipovsek et al. | |
| 4,743,256 A | 5/1988 | Brantigan | |
| 4,743,260 A | 5/1988 | Burton | |
| 4,759,766 A | 7/1988 | Buettner-Janz et al. | |
| 4,759,769 A | 7/1988 | Hedman et al. | |
| 4,761,406 A | 8/1988 | Flora et al. | |
| 4,763,644 A | 8/1988 | Webb | |
| 4,769,881 A | 9/1988 | Pedig et al. | |
| 4,772,287 A | 9/1988 | Ray | |

| | | | |
|---|---|---|---|
| 4,781,591 A | 11/1988 | Allen | |
| 4,790,303 A | 12/1988 | Steffee | |
| 4,798,213 A | 1/1989 | Doppelt | |
| 4,805,602 A | 2/1989 | Puno et al. | |
| 4,820,305 A | 4/1989 | Harms et al. | |
| 4,830,000 A | 5/1989 | Shutt | |
| 4,834,757 A * | 5/1989 | Brantigan | 623/17 |
| 4,843,112 A | 6/1989 | Gerhart et al. | |
| 4,848,327 A | 7/1989 | Perdue | |
| 4,851,008 A | 7/1989 | Johnson | |
| 4,863,476 A | 9/1989 | Shepperd | |
| 4,863,477 A | 9/1989 | Monson | |
| 4,865,603 A | 9/1989 | Noiles | |
| 4,877,020 A | 10/1989 | Vich | |
| 4,878,915 A * | 11/1989 | Brantigan | 623/17 |
| 4,903,882 A | 2/1990 | Long | |
| 4,904,260 A | 2/1990 | Ray et al. | |
| 4,904,261 A | 2/1990 | Dove et al. | |
| 4,905,671 A | 3/1990 | Senge et al. | |
| 4,911,718 A | 3/1990 | Lee et al. | |
| 4,913,144 A | 4/1990 | Del Medico | |
| 4,936,848 A | 6/1990 | Bagby | |
| 4,943,291 A | 7/1990 | Tanguy | |
| 4,944,744 A | 7/1990 | Ray | |
| 4,955,908 A | 9/1990 | Frey et al. | |
| 4,957,495 A | 9/1990 | Kluger | |
| 4,961,740 A | 10/1990 | Ray et al. | |
| 5,015,247 A * | 5/1991 | Michelson | 623/17 |
| 5,026,373 A | 6/1991 | Ray et al. | |
| D318,629 S | 7/1991 | Michelson | |
| 5,055,104 A | 10/1991 | Ray | |
| 5,084,050 A | 1/1992 | Draenert | |
| 5,122,130 A | 6/1992 | Keller | |
| 5,282,863 A | 2/1994 | Burton | |
| 5,489,307 A * | 2/1996 | Kuslich | 606/61 |

FOREIGN PATENT DOCUMENTS

| | | |
|---|---|---|
| DE | 1961531 | 7/1970 |
| DE | 24 46 039 | 4/1975 |
| DE | 31 01 333 A1 | 12/1981 |
| DE | 3101333 A1 | 12/1981 |
| DE | 31 32 520 A1 | 6/1982 |
| DE | 3132520 A1 | 6/1982 |
| DE | 32 19 575 | 12/1983 |
| DE | 35 05 567 A1 | 6/1986 |
| DE | 3505567 A1 | 6/1986 |
| DE | 36 08 163 A1 | 9/1987 |
| DE | 36 20 549 | 12/1987 |
| EP | 0 077 159 | 4/1983 |
| EP | 0 179 695 | 9/1985 |
| EP | 0 162 005 | 11/1985 |
| EP | 0 260 044 | 3/1988 |
| EP | 0303241 A2 | 2/1989 |
| EP | 0 307 241 | 3/1989 |
| ES | 283078 | 5/1985 |
| FR | 2 295 729 | 7/1976 |
| FR | 0 179 695 | 4/1986 |
| FR | 2 581 336 | 11/1986 |
| GB | 1 050 383 | 12/1966 |
| GB | 1291470 | 10/1972 |
| GB | 1492990 | 11/1977 |
| GB | 1531487 | 11/1978 |
| GB | 2076657 A | 12/1981 |
| GB | 2082754 A | 3/1982 |
| GB | 2126094 A | 3/1984 |
| GB | 2164277 A | 3/1986 |
| JP | 57-29348 | 2/1982 |
| JP | 60-31706 | 2/1985 |
| JP | 60-43984 | 3/1985 |
| JP | 61-122859 | 6/1986 |
| JP | 62-155846 | 7/1987 |
| SE | 106 101 | 7/1939 |
| SE | 108 101 | 7/1939 |
| SU | 662 082 | 5/1979 |
| SU | 1107854 | 8/1984 |
| SU | 1124960 | 11/1984 |
| SU | 1217374 | 3/1985 |
| SU | 1 148 610 | 7/1985 |
| SU | 1217374 | 3/1986 |
| SU | 1 225 543 | 4/1986 |
| SU | 1222254 | 4/1986 |
| WO | 84/01298 | 4/1984 |
| WO | 88/03781 | 6/1988 |

OTHER PUBLICATIONS

Cloward, Ralph B.; Ruptured Cervical Intervertebral Discs: Removal of Disc & Osteophytes & Anterior Cervical Interbody Fusion (A.C.I.F.): Codman; Signature Series 4.

Cloward, Ralph B.; Recent Advances in Surgery of the Cervical Spine; pp. 285-293; German Society For Neurosurgery: vol. 2 Cervical Spine Operations; Excerpta Medica.

Otero-Vich, Jose M.; Anterior Cervical Interbody Fusion with Threaded Cylindrical Bone; pp. 750-753; Journal of Neurosurgery, Nov. 1985, vol. 63, No. 5.

Hutter, Charles George; Spinal Stenosis and Posterior Lumbar Interbody Fusion; pp. 103-114; Clinical Orthopaedics and Related Research; No. 193; The Association of Bone and Joint Surgeons.

Lin, Paul M.; Posterior Lumbar Interbody Fusion; pp. 114-122; Charles C. Thomas; Springfield, Illinois.

Lin, Paul M.; Lumbar Interbody Fusion: Principles and Techniques in Spine Surgery; Techniques and Complications; pp. 81, 98, 120, 146, 173, 180-184, 204, 224, 225, 231; Aspen Publishers, Inc.; 1989.

Tan, S.B.; A Modified Technique of Anterior Lumbar Fusion with Femoral Cortical Allograft; pp. 83-93; The Journal of Orthopaedic Surgical Techniques, vol. 5, No. 3, 1990.

Muller, M.E.; Manual of Internal Fixation: Techniques Recommended by the AO Group; Second Edition, Expanded and Revised; pp. 3-20, 27-41, 53-58, 71-78, 94, 311, 320; Springer-Verlag; 1979.

Hierholzer, G.; Manual on the AO/ASIF Tubular External Fixator; pp. 85-91; Springer-Verlag; 1985.

Heim, Urs; Small Fragment Set Manual: Technique Recommended by the ASIF-Group; pp. 5-7, 10, 20, 21, 30; Springer-Verlag; 1974.

Harmon, Paul H.; Anterior Excision and Vertebral Body Fusion Operation for Intervertebral Disk Syndromes of the Lower Lumbar Spine: Three-to Five-Year Results in 244 Cases; pp. 107-127; Clinical Orthopaedics and Related, No. 26, J.B. Lippincott Company, 1963.

Harmon, Paul H.; A Simplified Surgical Technic for Anterior Lumbar Diskectomy and Fusion; Avoidance of Complications; Anatomy of the Retroperitoneal Veins; pp. 130-143; Clinical Orthopaedics and Related Research, No. 37, J.B. Lippincott Company, 1964.

Bullough, Peter G.; Atlas of Spinal Diseases; Figure 5.7; J.B. Lippencott Company; 1988.

Butts, M.K.; Biomechanical Analysis of a New Method for Spinal Interbody Fixation; 1987 Symposium, American Society of Mechanical Engineers, "Advance in Bioengineering", Boston, MA (Dec. 13-18, 1987).

Canale, S. Terry; Campbell's Operative Orthopaedics; vol. 3, 9th Edition; pp. 2191, 2216, 2459; Mosby, 1998.

Adams, et al.; Outline of Orthopaedics, Eleventh Edition; Trunk and Spine, p. 194.

Herkowitz, et al.; Principles of Bone Fusion; The Spine, Third Edition; Chapter 44, p. 1739.

Muschler, et al.; The Biology of Spinal Fusion; Spinal Fusion Science and Technique, Cotler and Coller, pp. 9-13.

Zindrick, et al.; Lumbar Spine Fusion: Different Types and Indications: The Lumbar Spine, vol. 1, Second Edition, pp. 588-593 (1998).

Gillingham, F.J., et al.; Automatic Patient Monitoring in th Ward; Brit. J. Surg., vol. 53, No. 10, pp. 864-866 (Oct. 1966).

Maloney, A.F.J., et al.; Clinical and Pathological Observations in Fatal H ad Injuries, Brit. J. Surg., V l. 56, No. 1, pp. 123-31 (Jan. 1969).

Harris, P., et al.; Spinal Deformity After Spinal Cord Injury; Paraplegia, vol. 6, No. 4, pp. 232-238 (Feb. 1969).

Gillingham, F.J., et al.; Head injuries; Proceedings of the 18th World Congress of the International College of Surgeons, Rome, pp. 68-71 (May 28-31, 1972).
Whatmore, W. J.; Sincipital Encephalomeningoceles; Brit. J. Surg., vol. 60, No. 4, pp. 261-270 (Apr. 1973).
Whatmore, W. J.; Meningloma Following Trauma; Brit. J. Surg., vol. 60, No. 6, pp. 496-498 (Jun. 1973).
Bagby, George W.; Wobbler Syndrome in Horses (the Ataxic Horse); Spokane County Medical Society Bulletin; Spring 1979.
Rathke, F.W., et al.; Surgery of the Spine; Atlas of Orthopaedic Operations, vol. 1, p. 137, W.B. Saunders, Co., Philadelphia (1979).
Albrektsson, T., et al.; Osseointegrated Titanium Implants; Acta. Orthop. Scand.; vol. 52;155-170 (1981).
Raveh, J., et al.; Neue Rekonstruktionsmoglichkelten des Unterkiefers bei knochemen Defekten nach Tumorresektionen; Der Chirurg vol. 53:459-467 (1982).
Crock, H. V.; Practice of Spinal Surgery; Springer-Verlag/Wien, New York (1983).
DeBowes, R.M., et al.; Study of Bovine . . . Steel Baskets; Transactions of the 29th Annual Meeting; Orthopaedic Research Society, vol. 8, p. 407, Mar. 8-10, 1983.
O'Neill, P., et al.; Spinal Meningoceles in Assocation with Neurofibromatosis; Neurosurgery, vol. 13, No. 1, pp. 82-84 (Jul. 1983).
Brandt, L., et al.; A Dowel Inserter for Anterior Cervical Interbody Fusion; J. Neurosurg. 61:793-794 (Oct. 1984).
Whatmore, W.J., et al.; The Coventry Cervical Spreader and Dowel Inserter; ACTA Neurochirurgica, vol. 70, FASC. 1-2 (1984).
Raveh, J., et al.; Use of the Titanium-coated Hollow Screw and Reconstruction Plate System in Bridging of Lower Jaw Defects; J. Oral Maxillofac Surg. 42:281-284 (1984).
Otero-Vich, Jose M.; Anterior Cervical Interbody Fusion with Threaded Cylindrical Bone; J. Neurosurg 63:750-753 (Nov. 1985).
Morscher, E., et al.; Die vordere Verplattung der Halswirbelsäule mit dern Hohlschrauben-Plattensystem aus Titanium, *Der Chirurg*, vol. 57, pp. 702-707 (1986) with English Translation.
Bagby, G.W.; Basket Implant Facilitates Spinal Fusion; Orthopedics Today, vol. 7, No. 10, (Oct. 1987).
Butts, M. K., et al.: Biomechanical Analysis of a New Method for Spinal Interbody Fixation; 1987 Symposium American Society of Mechanical Engineers, "Advances in Bioengineering", Boston, MA (Dec. 13-18, 1987).
Crawley et al.; A Modified Cloward's Technique for Arthr desis of the Normal Metacarpophelengeal Joint in the Horse; Veterinary Surgery, vol. 17, No. 3, pp. 117-127 (1988).
Raveh, J., et al.; Surgical Procedures for Reconstruction of the Lower Jaw Using the Titanium-Coated Hollow-Screw Reconstruction Plate System: Bridging of Defects; Otolaryngologic Clinics of North America; vol. 20, No. 3 (Aug. 1987).
Whatmore, W. J.; Proceedings of the Society of British Neurological Surgeons; Journal of Neurology, Neurosurgery, and Psychiatry, 50:1093-1100 (1987).
Goldthwaite, N., et al.; Toward Percutaneous Spine Fusion; Ch. 45; Lumbar Spine Surgery; C.V. Mosby Company, pp. 512-522 (1987).
Bagby, G.W.; Arthrodesis by the Distraction-Compression Method Using a Stainless Steel Implant; Orthopedics, vol. II, No. 6, pp. 931-934 (Jun. 1987).
Itoman, M., et al.; Banked Bone Grafting for Bone Defect Repair—Clinical Evaluation of Bone Union and Graft Incorporation; J. Jpn. Orthop. Assoc. 62:461-469 (1988).

Kane, W.J.; Direct Current Electrical Bone Growth Stimulation for Spinal Fusion; Spine, vol. 13, No. 3, pp. 363-365 (Mar. 1988).
Arnold, David M.; State of the Art Reviews: Pedicle Fixation of the Lumbar Spine; pp. 176-200, Hanley & Belfus, Inc., 1992.
North American Spine Society Second Annual Meeting, Jun. 25-28, 1987.
Cloward, Ralph B.; The Treatment of Ruptured Lumbar Intervertebral Discs by Vertebral Body Fusion; J Neurosurg. 10; pp. 154-167; 1953.
Morscher, E. et al.; The Anterior Plating of the Cervical Spine with the Titanium Hollow Screw System; Surgeon 57; 702-707; 1986.
White, Arthur H.; Lumbar Spine Surgery: Some Opinions of General Orthopedists and Superspecialists; pp. 11-15; 27; 30; 35-45; 265-268; 1987.
Olerud, Sven et al.; Transpedicular Fixation of Thoracolumbar Verterbral Fractures; No. 227; Feb. 1988; pp. 44-51.
Dick, Walter; Internal Fixation of Thoracic and Lumbar Spine Fractures; Hans Huber Publishers; pp. 11, 39, 44-46, 70-72, and 93.
Edeland, H.G.; Open Reduction of Central Compression Fractures of the Tibial Plateau, Preliminary Report of a New Method and Device Arrangement; Acta orthop. scand. 47, 1976; pp. 686-689.
Daniaux, H.; Transpedikuläre Reposition und Spongiosaplastik bei Wirbelkörperbrüchen der Unteren Brust- und Lendenwirbelsäule; Unfallchirurg No. 89, Springer-Verlag, 1986; pp. 197-213; with translation.
Nicola, Nikolaus et al.; Vertebral Hemangioma: Retrograde Embolization-Stabilization With Methyl Methacrylate; Surg Neurol 1987; No. 27; pp. 481-486.
Radiological Society of North America; RSNA Scietific Program, 74th Scientific Assembly and Annual Meeting.
Galibert, P. et al.; Note Préliminaire sur le Traitement des Angiomes Vertébraux Par Vertébroplastie Acrylique Percutanée; Neurochirurgie; No. 33; 1987; pp. 166-168; with translation.
Blauth et al.; Therapeutic Concept and Results of Operative Treatment in Acute Trauma of the Thoracic and Lumbar Spine: The Hannover Experience; Raven Press, Ltd. New York; 1987.
Carlson et al.; The Use of Methylmethacrylate in Repair of Neoplastic Lesions in Bone; Radiology 112:43-46; 1974.
Harrington, Kevin D.; The Use of Methylmethacrylate for Vertebral-Body Replacement and Anterior Stabilization of Pathological Fracture-Dislocations of the Spine due to Metastatic Malignant Disease; The Journal of Bone and Joint Surgery, Incorporated; 1981.
Kennedy, William R.; Fractures of the Tibial Condyles; Clinical Orthopaedics and Related Research; No. 134; 1978.
Malawer et al.; Effect of Cryosurgery and Polymethyl Methacrylate on a Tumor Cavity: Evaluation of Bone Necrosis and Bone Graft Incorporation in a Dog Model; 1988.
Richter-Turtur et al.; Das Problem der Belastungsstabilitat bei pathologischen Frakturen (The Problem of Load Stability in Pathological Fractures); Akt. Traumatol. 14 Georg Thieme Verlag Stuttgart—New York; 1984.
Schatzker, Joseph; Fractures of the Tibial Plateau; text book; 1987.
Steffee et al.; Reduction and Stabilization of Grade IV Spondylolisthesis; Clinical Orthopaedics and Related Research—No. 227; 1988.
Steffee et al.; Segmental Spine Plates with Pedical Screw Fixation; Clinical Orthopaedics and Related Research; 1986.
Yuan-zhang et al.; Os Calcis Fracture Treated by Percutaneous Poking Reduction and Internal Fixation; Chinese Medical Journal; 1984.

* cited by examiner

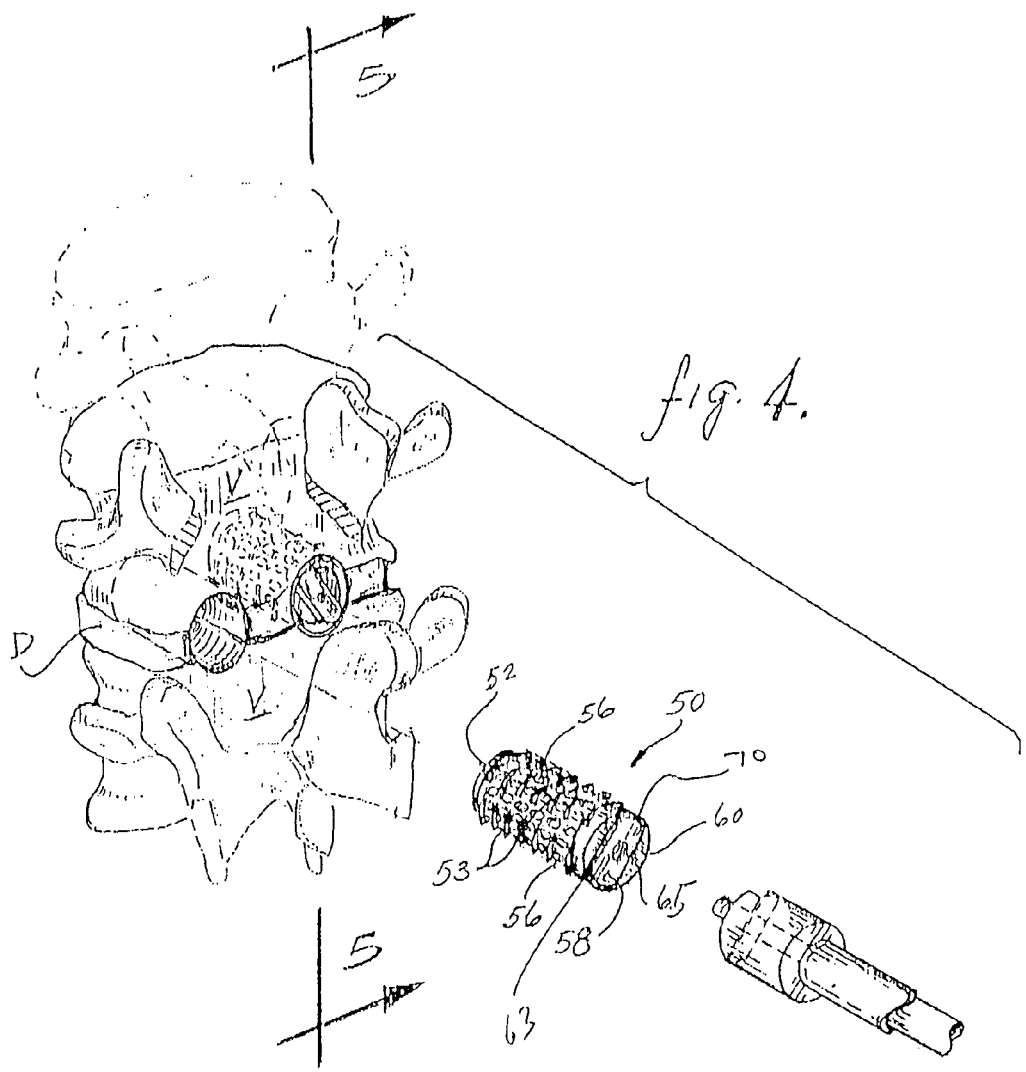

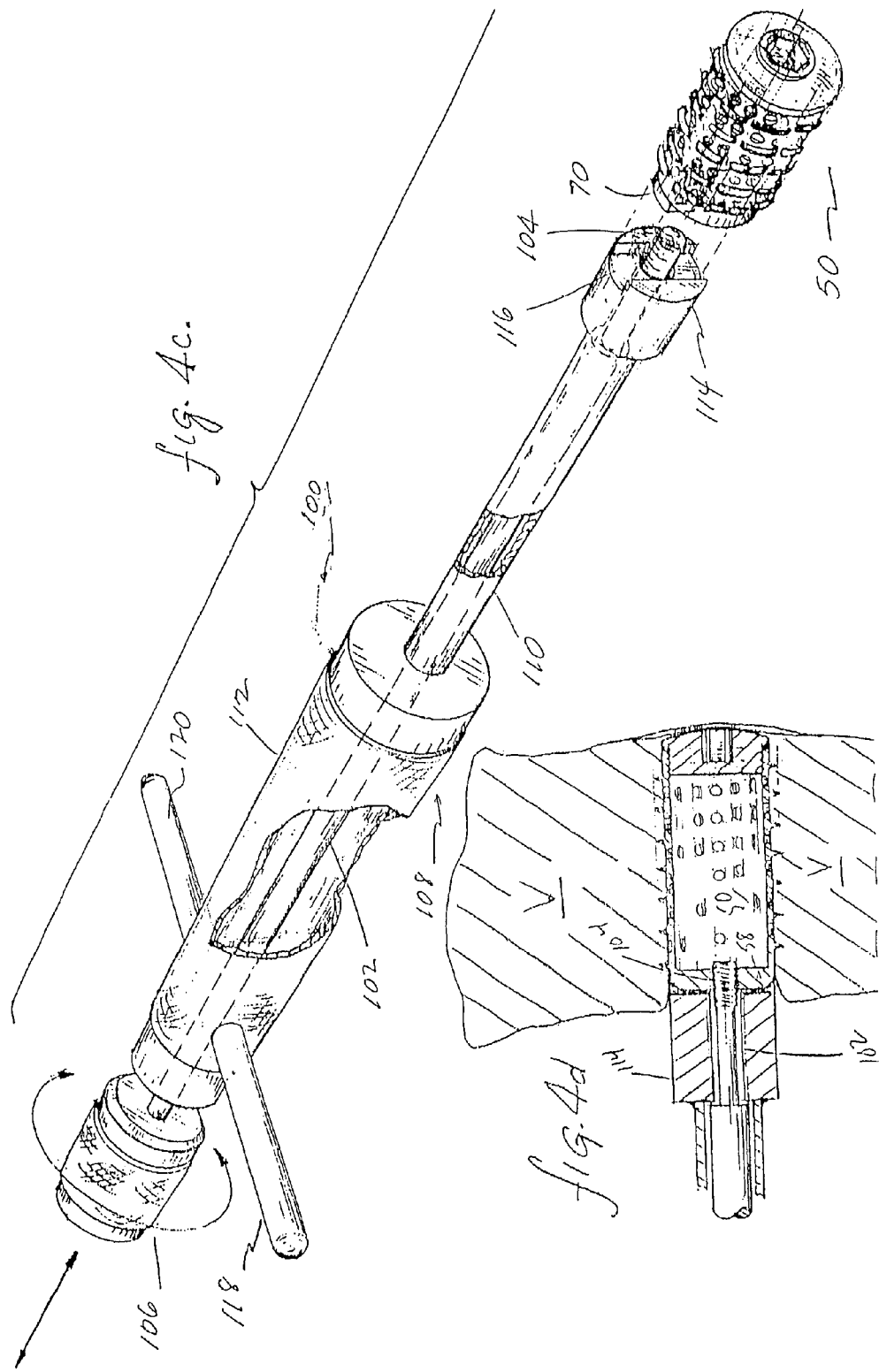

APPARATUS FOR INSERTING SPINAL IMPLANTS

This application is a division of application Ser. No. 07/968,240, filed on Oct. 29, 1992, U.S. Pat. No. 5,741,253 which is a continuation of Ser. No. 07/698,674, filed May 10, 1991, now abandoned which is a divisional of Ser. No. 07/205,935, filed on Jun. 13, 1988, now issued U.S. Pat. No. 5,015,247.

BACKGROUND

The present invention relates to an artificial fusion implant to be placed into the intervertebral space left after he removal of a damaged spinal disc.

The purpose of the present invention is to provide an implant to be placed within the intervertebral disc space and provide for the permanent elimination of all motion at that location. To do so, the device is space occupying within the disc space, rigid, self-stabilizing to resist dislodgement, stabilizing to the adjacent spinal vertebrae to eliminate local motion, and able to intrinsically participate in a vertebra to vertebra bony fusion so as to assure the permanency of the result.

At present, following the removal of a damaged disc, either bone or nothing is placed into the space left. Placing nothing in the space allows the space to collapse which may result in damage to the nerves; or the space may fill with scar tissue and eventually lead to a rehemiation. The use of bone is less than optimal in that the bone obtained from the patient requires additional surgery and is of limited availability in its most useful form, and if obtained elsewhere, lacks living bone cells, carries a significant risk of infection, and is also limited in supply as it is usually obtained from accident victims. Furthermore, regardless of the source of the bone, it is only marginal structurally and lacks a means to either stabilize itself against dislodgement, or to stabilize the adjacent vertebrae.

A review of related prior art will demonstrate the novelty of the present invention.

There have been an extensive number of attempts to develop an acceptable disc prosthesis (an artificial disc). Such devices by design would be used to replace a damaged disc and seek to restore the height of the interspace and to restore the normal motion of that spinal joint. No such device has been found that is medically acceptable. This group of prosthetic or artificial disc replacements, seeking to preserve spinal motion and so are different from the present invention, would include:

U.S. Pat. No. 3,867,728 STUBSTAD—describing a flexible disc implant.

U.S. Pat. No. 4,349,921 KUNTZ—describing a flexible disc replacement with file like surface projections to discourage device dislocation.

U.S. Pat. No. 4,309,777 PATIL—describing a motion preserving implant with spiked outer surfaces to resist dislocation and containing a series of springs to urge the vertebrae away from each other;

U.S. Pat. No. 3,875,595 FRONING—describing a motion preserving bladder like disc replacement with two opposed stud-like projections to resist dislocation.

U.S. Pat. No. 2,372,622 Fassio (French)—describing a motion preserving implant comprising complimentary opposed convex and concave surfaces.

In summary then, these devices resemble the present invention only in that they are placed within the intervertebral space following the removal of a damaged disc. In that they seek to preserve spinal motion, they are diametrically different from the present invention which seeks to permanently eliminate all motion at that spinal segment.

A second related area of prior art includes those devices utilized to replace essentially wholly removed vertebra. Such removal is generally necessitated by extensive vertebral fractures, or tumors, and is not associated with the treatment of disc disease. While the present invention is to be placed within the disc space, these other vertebral devices cannot be placed within the disc space as at least one vertebra has already been removed such that there no longer remains a "disc space." Furthermore, these devices are limited in that they seek to perform as temporary structural members mechanically replacing the removed vertebra (not a removed disc), and do not intrinsically participate ih supplying osteogenic material to achieve cross vertebrae bony fusion. Therefore, again unlike the present invention which provides for a source of osteogenesis, use of this group of devices must be accompanied by a further surgery consisting of a bone fusion procedure utilizing conventional technique. This group consisting of vertebral struts rather than disc replacements would include the following:

U.S. Pat. No. 4,553,273 WU—describing a turnbuckle like vertebral strut.

U.S. Pat. No. 4,401,112 REZAIAN—describing a turnbuckle like vertebral strut with the addition of a long stabilizing staple that spans the missing vertebral body.

U.S. Pat. No. 4,554,914 KAPP—describing a large distractible spike that elongates with a screw mechanism to span the gap left by the removal of a entire vertebra and to serve as an anchor for acrylic cement which is then used to replace the missing bone vertebra.

U.S. Pat. No. 4,636,217 OGILVIE—describing a vertebral strut mechanism that can be implanted after at least one vertebra has been removed and which device consists of a mechanism for causing the engagement of screws into the vertebra above and the vertebra below the one removed.

In summary then, this group of devices differs from the present invention in that they are vertebra replacements struts, do not intrinsically participate in the bony fusion, can only be inserted in the limited circumstances where an entire vertebra has been removed from the anterior approach, and are not designed for, or intended to be used for the treatment of disc disease.

A third area of prior art related to the present invention includes all devices designed to be applied to one of the surfaces of the spine. Such devices include all types of plates, struts, and rods which are attached by hooks, wires and screws. These devices differ significantly from the present invention in that they are not inserted within the disc space, and furthermore do not intrinsically participate in supplying osteogenic material for the fusion.

Therefore, with these devices where permanent spinal immobilization is desired an additional surgery consisting of a spinal fusion performed by conventional means or the use of supplemental methylmethacrylate cement is required. Such devices applied to the spine, but not within the disc space, would include the following:

U.S. Pat. No. 4,604,995—STEPHENS—describing a "U" shaped metal rod attached to the posterior elements of the spine with wires to stabilize the spine over a large number of segments.

U.S. Pat. No. 2,677,369—KNOWLES—describing a metal column device to be placed posteriorly along the lumbar spine to be held in position by its shape alone and to block pressure across the posterior portions of the spinal column by locking the spine in full flexion thereby shifting the maximum weight back onto the patient's own disc.

Other devices are simply variations on the use of rods (e.g. Harrington Luque, Cotrel-Dubosset, Zielke), wires or cables (Dwyer), plates and screws (Steffee), or struts (Dunn, Knowles).

In summary, none of these devices are designed or can be used within the disc space, do not replace a damaged disc, and do not intrinsically participate in the generation of a bony fusion.

Another area of related prior art to be considered is that of devices designed to be placed within the vertebral interspace following the removal of a damaged disc, and seeking to eliminate further motion at that location.

Such a device is contained in U.S. Pat. No. 4,501,269 BAGBY—describing an implantable device and limited instrumentation. The method employed is as follows: a hole is bored transversely across the joint and Lihen a hollow metal basket of larger diameter than the hole is then pounded into the hole and then filled with the bone debris generated by the drilling.

While the present invention (device, instrumentation, and method) may appear to bear some superficial resemblance to the BAGBY invention, it is minimal, while the differences are many fold and highly significant. These differences include the following:

1. Safety—The present invention provides for a system of completely guarded instrumentation so that all contiguous vital structures (e.g. large blood vessels, neural structures) are absolutely protected. Said instrumentation also makes overpenetration by the drill impossible. Such overpenetration in the cervical spine, for example, would result in the total paralysis or death of the patient. In the thoracic spine, the result would be complete paraplegia. In the lumbar spine, the result would be paraplegia or a life-threatening perforation of the aorta, vena cava, or iliac vessels. The present invention is atraumatically screwed into place while the BAGBY device, in contradistinction, is pounded into position. BAGBY describes that the implant is significantly larger in size than the hole drilled and must be pounded in. This is extremely dangerous and the pounding occurs, directly over the spinal cord which is precariously vulnerable to percussive injury. Furthermore, while it is possible, for example in the lumbar spine, to insert the present invention away from the spinal cord and nerves, the BAGBY device must always be pounded directly towards the spinal cord.

Furthermore, since the BAGBY device is pounded into a smooth hole under great resistance, and lacking any specific design features to secure it, the device is highly susceptible to forceful ejection which would result in great danger to the patient and a clinical failure. The present invention, in contradistinction, is securely screwed into place, and possesses highly specialized locking threads to make accidental dislodgement impossible. Because of the proximity of the spinal cord, spinal nerves, and blood vessels, any implant dislodgement as might occur with the BAGBY device might have catastrophic consequences.

2. Broad applicability—The BAGBY device can only be inserted from the front of the vertebral column, however, the present invention can be utilized in the cervical, thoracic, and lumbar spine, and can be inserted from behind (posteriorly) in the lumbar spine. This is of great importance in that the purpose of these devices is in the treatment of disc disease and probably greater than 99 percent of all lumbar operations for the treatment of disc disease are performed from behind where the present invention can easily be utilized, but the BAGBY device, as per his description, cannot.

3. Disc removal—The BAGBY invention requires the complete removal of the disc prior to the drilling step, whereas the present invention eliminates the laborious separate process of disc removal and efficiently removes the disc and prepares the vertebral end plates in a single step.

4. Time required—The present invention saves time over the BAGBY invention in that time is not wasted laboring to remove the disc prior to initiating the fusion. Also, since with the present invention the procedure is performed through a system of guarded instrumentation, time is not wasted constantly placing and replacing various soft tissue retractors throughout the procedure.

5. Implant stability—Dislodgement of the implant would be a major source of device failure (an unsuccessful clinical result), and might result in patient paralysis or even death. As discussed, the BAGBY device lacks any specific means of achieving stability and since it is pounded in against resistance to achieve vertebral distraction, it is susceptible to forceful dislodgement by the tendency of the two distracted vertebrae, to return to their original positions squeezing out the device. The present invention however is screwed into place. As there is no unscrewing force present between the vertebrae and compression alone cannot dislodge the implant, the implant is inherently stable by its design. Furthermore, the threads of the present invention are highly specialized in that they are periodically interrupted such that the tail ends of each of the tabs so formed are blunted and twisted so as to resist accidental unscrewing. The removal of an implant with such "locking threads" requires the use of a special extractor included within the instrumentation. The stability of the present invention is still further enhanced, again in contradistinction to the BAGBY device, by the presence of a "bone ingrowth" surface texturing, which both increases the friction of the fit and allows for the direct growth of the vertebral bone into the casing of the implant itself.

6. Spinal stability—The present invention is not only self-stabilizing, it also provides stability to the adjacent vertebrae in at least three ways that the BAGBY device cannot. First, the BAGBY device is placed transversely across the joint in the center, leaving both vertebrae free to rock back and forth over this round barrel shaped axis, much like a board over, a barrel, being used for a seesaw.

Secondly, as the BAGBY device lacks any specific design features to resist sliding, it may actually behave as a third body allowing the translation of the vertebrae relative to the device and to each other.

Thirdly, any device can only provide stability if it remains properly seated. The present invention is inherently stable, and therefore assures that it will stabilize the adjacent vertebrae; rather than, as with the BAGBY device, where the instability of the spine to be treated may instead cause a dislocation of the implant, with further loss of spinal stability.

7. The collapse of the interspace—While both the present invention and the BAGBY device can be fabricated to withstand the compression forces within the interspace, the interspace may nevertheless collapse under the superincumbent body weight as the implant settles into the vertebral bone. This is related to the load per unit area. Again the present invention is superior to the BAGBY device in at least four ways. First, the present invention offers considerably greater surface area to distribute the load. Secondly, while the BAGBY device is placed centrally, the present device is placed bilaterally where the bone tends to be more cortical and much stronger out towards the rim. Thirdly, the present invention supports the load achieving an "I" beam effect, whereas the BAGBY implant does not. Fourthly, it is not pressure alone that causes the collapse of the bone adjacent to the implant, but also bony erosion that is caused by the motion under pressure of the implant against the bone. As discussed in item #6 above, the present invention alone is highly resistant to such motion, again diminishing the likelihood of erosion and interspace collapse.

8. Bone ingrowth surface texturing—The present invention has a surface treatments of known and conventional technology to induce the growth of bone from the vertebrae directly into the casing material of the implant itself. The BAGBY device has no similar feature.

9. Fusion mass—The BAGBY invention calls for removing the disc and then drilling a hole between the adjacent vertebrae. The bony debris so generated is then put into the device. The present invention takes a core of pure bone producing marrow from the iliac crest, and then by use of a special press forcibly injects the device with an extremely dense compressed core of that osteogenic material until the material itself virtually extrudes from every cell of the implant.

10. The probability of achieving fusion—The fusion rate within the spine is known to be related directly to the amount of exposed vascular bone bed area, the quality and quantity of the fusion mass available, and the extent of the stabilization obtained with all other factors being hold constant. It would then be anticipated, that the fusion rate would be superior with the present invention as compared to the BAGBY device, because of optimal implant stability (#5), optimal spinal stability (#6), bone ingrowth surface treatment (#8), superior fusion mass (#9), and the greater exposed vertebral bony surface area (#7).

The last area of prior art possibly related to the present invention and therefore, to be considered related to "BONY INGROWTH", and patents either describe methods of producing materials and or materials or devices to achieve the same. Such patents would include:

U.S. Pat. Nos. 4,636,526 (DORMAN), No. 4,634,720 (DORMAN), No. 4,542,539 (ROWE), No. 4,405,319 (COSENTINO), No. 4,439,152 (SMALL), No. 4,168,326 (BROEMER), No. 4,535,485 (ASIIMAN), No. 3,987,499 (SCHARBACH), No. 3,605,123 (HAHN), No. 4,655,777 (DUNN), No. 4,645,503 (LIN), No. 4,547,3901 (ASHMAN), No. 4,608,052 (VAN KAMPEN), No. 4,698,375 (DORMAN), No. 4,661,536 (DORMAN), No. 3,952,334 (BOKROS), No. 3,905,047 (LONG), No. 4,693,721 (DUCHEYNE), No. 4,070,514 (ENTHERLY).

However, while the present invention would utilize bone ingrowth technology, it would do so with conventional technology.

In summary then, the present invention, instrumentation, and method, alone provides for a one stage discectomy, fusion, and interbody internal spinal fixation; that being performed more quickly, with greater safety, and more effectively, for all of the aforementioned reasons than is possible with any other known art.

BRIEF SUMMARY OF THE INVENTION

The present invention comprises a series of artificial implants, the purpose of which is to participate in, and directly cause bone fusion across an intervertebral space following the excision of a damaged disc. Such implants are structurally load bearing devices, stronger than bone, capable of withstanding the substantial forces generated within the spinal interspace. Such devices have a plurality of macro sized cells and openings, which can be loaded with fusion promoting materials, such as autogenous bone, for the purpose of materially influencing the adjacent vertebrae to form a bony bond to the implants and to each other. The implant casing may be surface textured or otherwise treated by any of a number of known technologies to achieve a "bone ingrowth surface" to further enhance the stability of the implant and to expedite the fusion.

Further, said devices are so configured and designed so as to promote their own stability within the vertebral interspace and to resist being dislodged, and furthermore, to stabilize the adjacent spinal segments.

The apparatus for preparing the vertebrae for insertion of the implant is also disclosed, such instrumentation and method allowing for the rapid and safe removal of the disc, preparation of the vertebrae, performance of the fusion, and internal stabilization of the spinal segment.

DISCUSSION OF THE INSTRUMENTATION

The concept of performing various aspects of this surgery are not entirely new. Drills are frequently placed through hollow, tubular guards to protect the adjacent soft tissues. A set of instruments developed by Ralph Cloward utilizes such a tubular drill guard on a larger scale, for the purpose of drilling into the cervical spine. However, this inventor is unaware of any set of instruments, system, or procedure designed to allow the entire surgical procedure beyond the initial exposure, to be performed blindly and with complete safety through a fixed sheath apparatus. Specific design features which combine to make this uniquely possible are as follows:

1. The availability of the specific implant.
2. The end of all the penetrating instrumentation is blunt faced.
3. All of the instruments have been stopped out at a predetermined depth to avoid overpenetration.
4. The design of the external sheath conforms to the spacial limitations of the specific surgical site.
5. The design and use of a second or inner sheath allows for the difference in size between the inside diameter of the outer sheath, and the outside diameter of the drill itself. This difference being necessary to accommodate the sum of the distraction to be produced, and the depth of the circumferential threading present on the implant.
6. A specially designed drill bit with a central shaft recess allows for the safe collection of the drilling products, which can then be removed without disturbing the outer sheath by removing the drill bit and inner sheath as a single unit.
7. A specially designed trephine for removing a core of bone slightly smaller in diameter than the internal diameter of the implant cavity itself, however of a greater length.
8. A specially designed press for forcefully compressing and injecting the long core of autogenous bone into the implant, such that it extrudes through the implant itself.
9. A specially designed driver extractor, which attaches to the implant and allows the implant to be either inserted or removed without itself dissociating from the implant, except by the deliberate disengagement of the operator.

OBJECTS OF THE PRESENT INVENTION

It is an object of the present invention to provide an improved method of performing a discectomy, a fusion, and an internal stabilization of the spine, and specifically, all three of the above simultaneously and as a single procedure.

It is another object of the present invention to provide an improved method of performing a discectomy, a fusion, and an internal stabilization of the spine, which is both quicker and safer than is possible by previous methods.

It is another object of the present invention to provide an improved method of performing a discectomy, a fusion, and an internal stabilization of the spine, to provide for improved surgical spinal implants.

It is another object of the present invention to provide an improved method of performing a discectomy, a fusion, and an internal stabilization of the spine, which provides for an improved system of surgical instrumentation to facilitate the performance of the combined discectomy, fusion, and internal spinal stabilization.

It is another object of the present invention to provide an improved method performing a discectomy, a fusion, and an internal stabilization of the spine.

These and other objects of the present invention will be apparent from review of the following specifications and the accompanying drawings.

BRIEF DESCRIPTION OF THE DRAWINGS

FIG. 1 is a perspective view of the driver and sheath and its orientation to a vertebral structure.

FIG. 4 is a perspective view of a cylindrical implant and vertebrae structure.

FIG. 4A is a perspective view of one preferred embodiment of the implant.

FIG. 4B is a cross sectional view of the implant of FIG. 4A.

FIG. 4C is the driving and insertion equipment for the implant of FIG. 4A.

FIG. 4d is a side sectional view of the driver and implant between vertebrae.

DETAILED DESCRIPTION OF THE DRAWINGS

Figures 1, 1A:
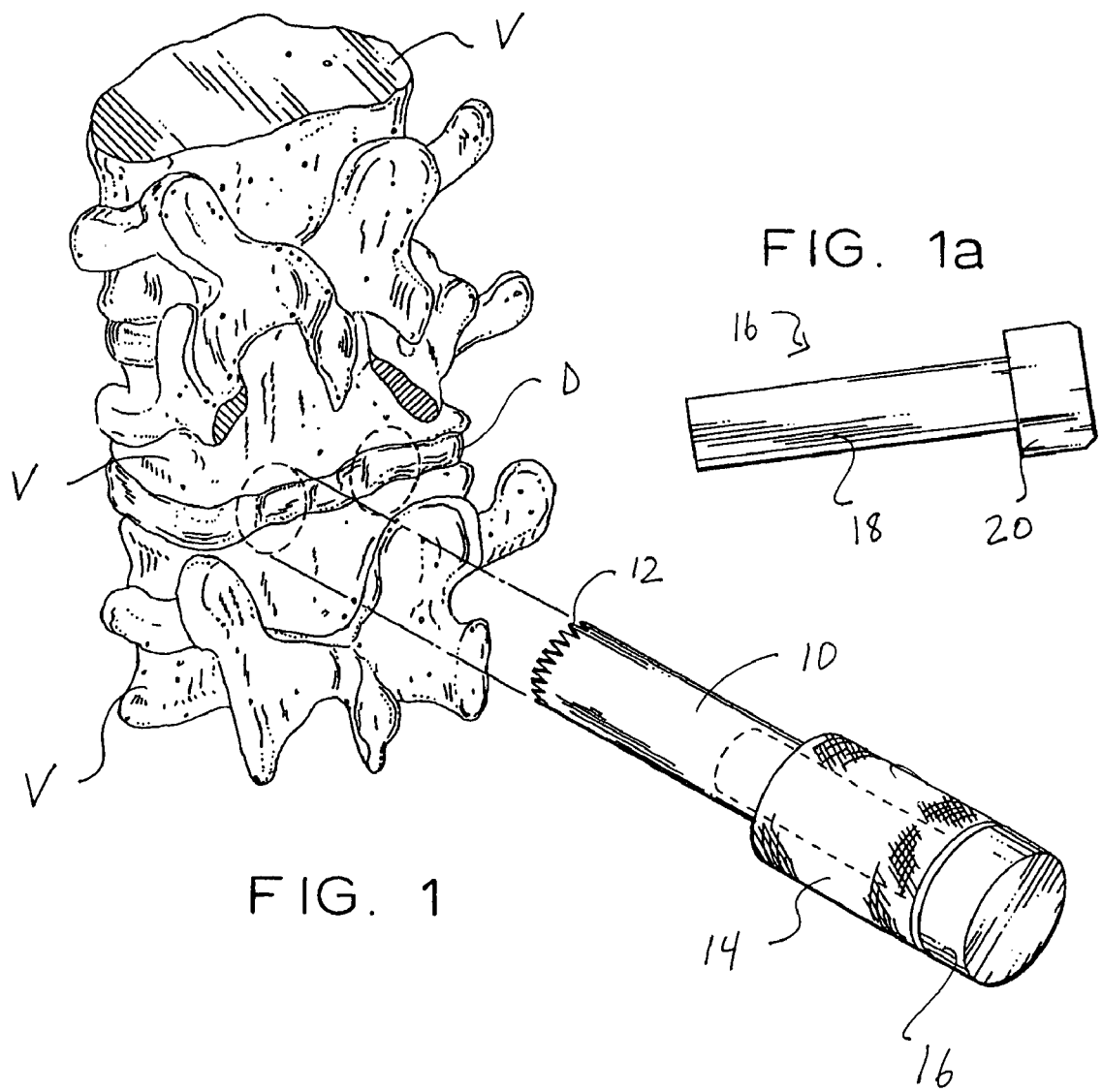
FIG. 1 is a partial view of the vertebrae structure with the driver and outer sheath assembly of the present invention.
FIG. 1A is a perspective view of the driver member for the outer sheath.

Referring to FIG. 1 a vertebrae structure comprising two vertebrae V and a disc D between the two vertebrae, is shown. A hollow tubular drill sleeve 10 has teeth 12 at its lower end. The sleeve 10 has an enlarged diameter upper portion 14.

A driver 16, shown in FIG. 1A, consists of a solid tubular member 18 and an increased diameter head 20. The external diameter of the solid tubular member 18 is slightly smaller than the inside diameter of the hollow tubular drill sleeve 10 and has a length that is substantially shorter than the overall length of the hollow tubular drill sleeve 10.

The drill sleeve 10 is made of metal in order to be driven into the vertebrae V and be held in place by the teeth 12 of the drill sleeve 10.

Figure 2:
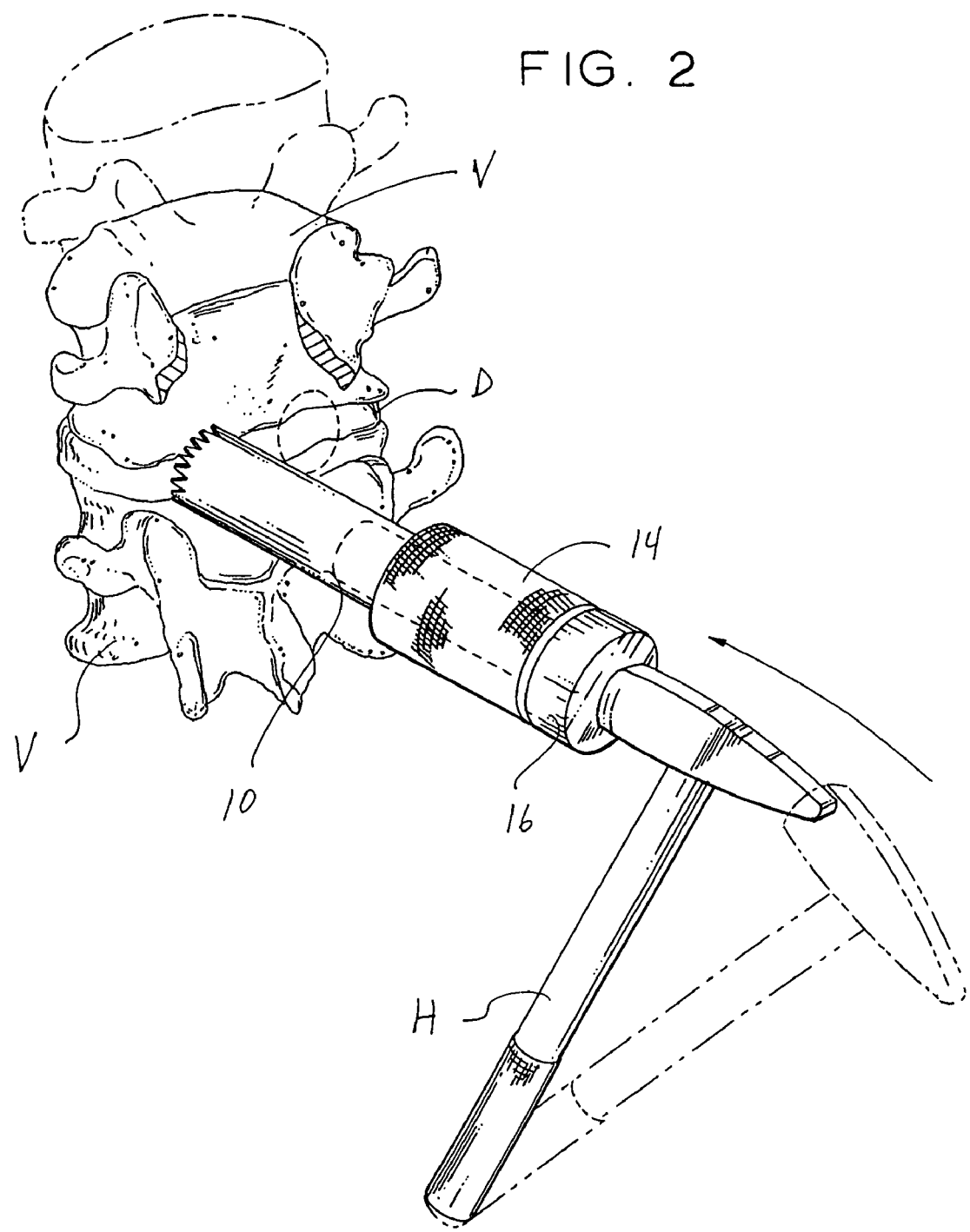
FIG. 2 is a perspective view of the outer sheath being inserted into the vertebrae structure.

Referring to FIG. 2 the drill sleeve 10 with the driver 16 installed is shown being driven into two vertebrae V on either side of a disc D by hammer H.

Figure 3:
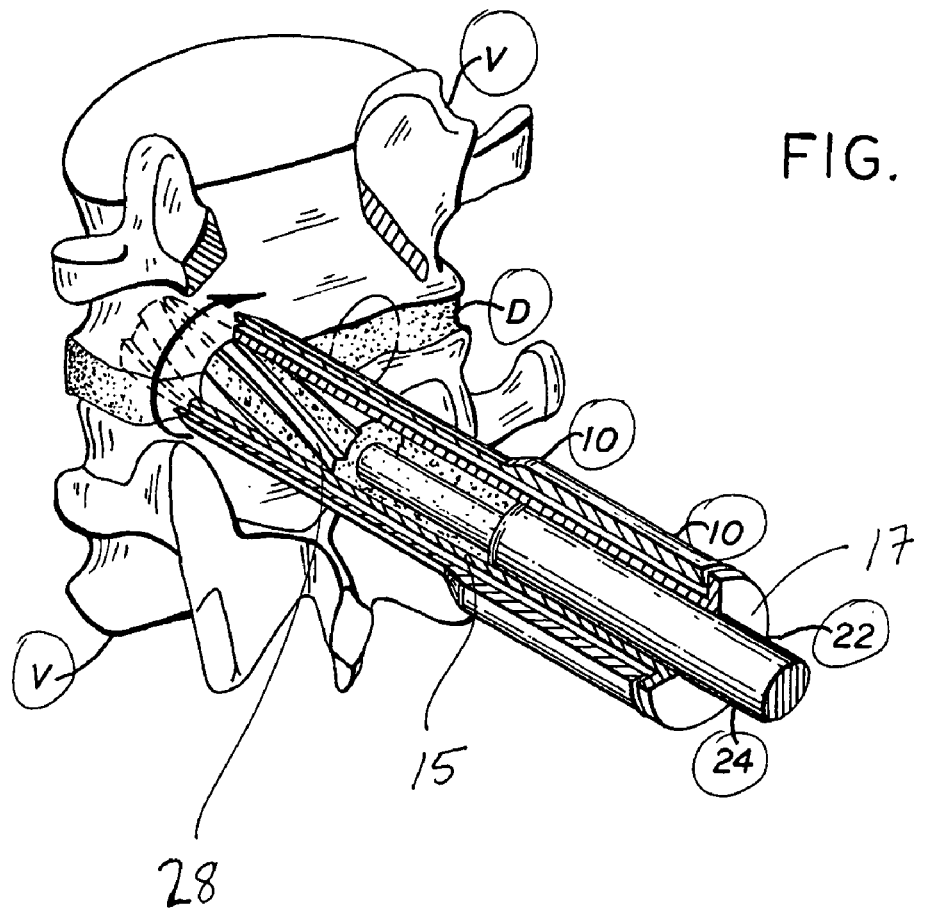
FIG. 3 is a perspective view of the outer sheath and inner sheath assembly, with the drill bit of the present invention.
Figure 3A:
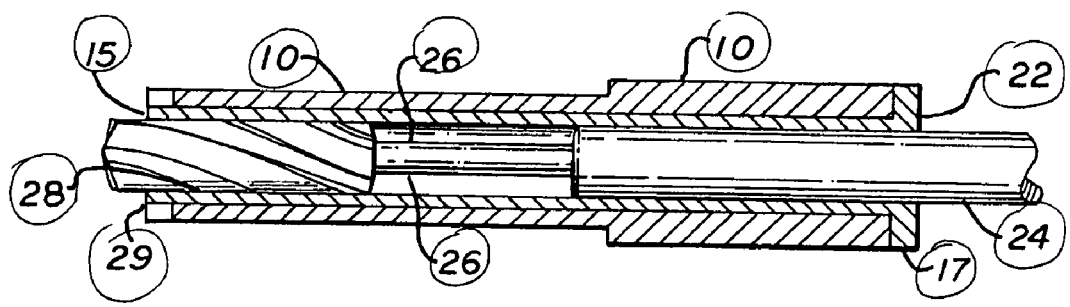
FIG. 3A is a side sectional view of the collar and drill bit of FIG. 3.
Figure 5:
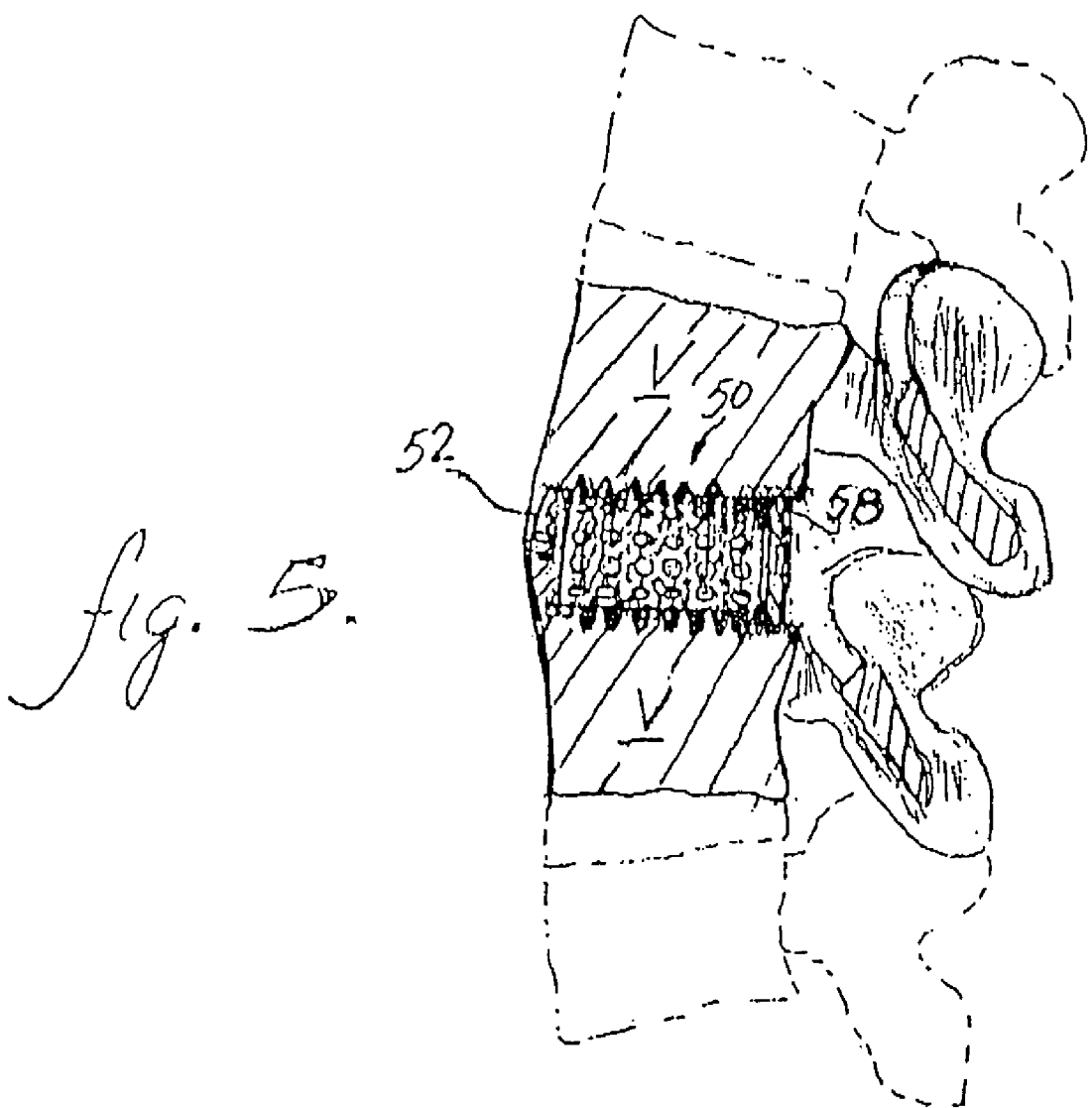
FIG. 5 is a sectional view of the vertebrae structure, taken along lines 5-5 of FIG. 4.

Referring to FIGS. 3 and 3a the drill assembly is shown. In FIG. 3 the drill sleeve 10 is illustrated in the two vertebrae V, straddling the disc D.

The retaining sleeve 15 has an outside diameter slightly smaller than the inside diameter of the drill sleeve 10, and a length substantially the same length as the drill sleeve 10. The retaining sleeve 15 has a collar 17 at its upper end for engaging the top of the drill sleeve 10.

The drill 22 comprises an upper portion 24, a central recessed portion 26 and a lower cutting drill portion 28. The upper 24 and lower portion 28 of the drill 22 have the same outside diameter. The drill 24 has a collar 30 attached to the upper portion 24 of the drill 22.

The outside diameter of the drill 22 is slightly smaller than the inside diameter of the retaining sleeve 15. The length of the drill, from the collar 30 to the end of the drill bit, is such that a predetermined portion of the drill bit 22 extends beyond the end 29 of the sleeve when fully inserted.

Referring to FIG. 4, a cylindrical embodiment of the present invention is shown, one implant positioned in the opening in the vertebrae and disc formed by the drill 22, and a second implant shown prior to implantation.

The cylindrical implant 50 comprises a hollow tubular member which in the preferred embodiment is made of an ASTM surgically implantable material, and preferably Titanium. The cylindrical implant 50 is closed at one end 52 and open at the other end 54. The outer cylindrical implant 50 has a series of macro-sized openings 56 through the side walls of the cylindrical member 50. A series of external threads 53 are formed on the circumference of the cylindrical implant 50. The threads 53 are locking threads having a series of interjections. the ends of which are blunted and twisted so as to resist unscrewing.

The open end 54 of the cylindrical implant 50 has an internal thread 51 for receiving a complementary cap 52 which has an external thread 58 for engaging the internal threads 51 of the cylindrical member 50. The cap 52 has a hexagonal opening 59 for use with an allen wrench for tightening the cap. A driver engaging element 70 is located on the rear surface 60 of the implant. The driver engaging element 70 comprises a raised rectangular portion 63 and a central threaded opening 65, for engaging the driver apparatus, shown in FIG. 4c and FIG. 4d. The driving equipment 100 comprises a central tubular rod 102 having a thread fitting into opening 65 in the implant. An enlarged knurled knob 106 is affixed to the other end of the rod 102 for ease in turning. The central rod 102 is enclosed within a hollow tubular member 108, having a narrow lower portion 110 and an increased diameter upper portion 112. At the end of the lower portion 110 is a attachment member 114, having a generally rectangular depression 116 for complementing the driver engaging element 70 of the implant 50. A pair of handles 118 and 120 extend perpendicular from the upper position 112 of the tubular member 108 to assist in turning the driver 100.

The operation is performed in the following manner: (Example Lumbar Spine Posterior Approach) A skin incision is made directly over the interspace to be operated on. The dissection is carried down along side of the superspinous and intraspinous ligaments preserving those structures. A semi hemi laminotomy is performed at the upper level, removing sufficient bone to allow access into the interspace. The ligament flavum is removed and then the dural sac is protected by retracting it medially along with the traversing (inferior) nerve root. The superior nerve root or the root exiting beneath the pedicle at the level above is visualized and protected.

At this time the drill sleeve 10 is placed into the spinal canal with both nerve roots directly inspected and protected. The drill sleeve 10 is imbedded by teeth 12 spanning the disc space from the midline over and it is seated into the two vertebrae V across the disc D space by using a driver 20. Once this is done, the driver 20 is removed and a retaining sleeve 15 is placed through the drill sleeve 10. Once seated, sleeve 10 provides absolute protection to the dural sac and nerve roots as the remaining surgery is performed entirely through this sleeve.

The inner sleeve allows for the difference between the outside diameter of the drill 22 and the outside diameter of the threads 53 of the cylindrical implant 50. This then makes it possible to perform the entire operation through the Lumen of the imbedded outer sleeve despite the differences in diameter between the drill and the implant.

A drill 22 is then placed in the retaining sleeve 17. The drill 22 is of such a length that it can not penetrate more then 28 millimeters beyond the end of the drill sleeve 10. This, of course, could be varied and made smaller for enhanced safety. However at the present time 27 to 28 millimeters seems to be safe for probably 3 standard deviations of the population. The drill 22 is attached to a power unit and the drilling takes place.

The recessed central area between the reduced portion 26, allows for the accumulation of the debris generated by the drilling. At this time, leaving the outer sleeve firmly embedded, the retaining sleeve 17 is removed with the drill 22 as a single unit. All the vertebrae and disc debris that was generated during the drilling is contained within the recess and against the inside wall of the retaining sleeve 17 and can not come out within the spinal canal. Once the retaining sleeve 17 and drill 22 is out of the patient's operative field, all of the material so generated can be removed.

The next step is that a screw tap is put down through the drill sleeve 10. The tap also has a collar on it that will automatically stop the tap from extending beyond 28 millimeters of penetration. The tap itself has a blunt nose that would also avoid any perforation. The tap is then removed. The tap size has deliberately been selected so that it's inner root diameter is 1.3 millimeters greater than the outside diameter of the drill 22. This insures that the interspace will be distracted by at least that much once the implant is placed. The tap has its outside diameter 1.2 millimeters greater than its root diameter. The tap is removed and the space is now prepared to accept the cylindrical implant 50.

The Implant 50 is prepared by utilizing the trephine, a hollow drill, to obtain a core of pure cancellous bone from the patients iliac crest of slightly smaller diameter than the internal diameter of the implant but approximately 6 mm longer. The implant 50 is placed in a press like device like an ammo loader and the bone graft measuring approximately 32 millimeters is then compressed into the hollow body of the implant (26 mm) so that the bone graft fills the opening 54 and extends through the openings 56. The cap 60 is then screwed on to the implant 50 by use of an allen driver/wrench and the device is ready for implantation.

The inserter/remover is such that it lock onto the implant, so that the implant can be moved either clockwise or counterclockwise, screwed or unscrewed. The implant itself has for its root diameter the same exact root diameter as the tap which as already noted is already 1.3 millimeters greater than the drill and has an outside diameter, 1.5 millimeters greater than its root. This is also 0.3 millimeters greater than the threads' cut by the tap so that in inserting the device it is actually cutting through previously uncut bone helping to insure that it locks in firmly. The threads on the implant 50 are locking threads so that it is easier to screw the device in than for it to be unscrewed. However, with sufficient torque it is possible to extract the device if ones so desires.

Once the implant has been seated it is able to be inserted only 28 millimeters. Since the implant 50 is only 26 millimeters in length, this virtually guarantees that the implant 50 will be recessed into the vertebral bodies more than 2 millimeters and can not protrude into the spinal canal.

Similarly, the implants shown in FIG. 4b can be implanted. The implant in FIG. 4b is a modified solid, having extensive channeling throughout, and has no cap. A central opening 61 permits insertion of the bone graft material into the interior of the implant.

These implants have a surface configuration such as to induce bone ingrowth through the implant, and into the wall of the vertebrae in effect inducing fusion from one vertebra in joint to the other, thereby eventually making the implant itself superfluous as the bone would do the work.

The implant itself, because of its being made of stronger material than bone, would provide structural support to the two vertebrae while awaiting bone ingrowth. Once the bone ingrowth occurred, however, the implant would be firmly and permanently fixed in place.

As, shown in FIG. 4, more than one implant is inserted into the disc space, thereby preventing the rocking motion that would result in the difficulties referred to above in the discussion of the Bagby patent.

While the invention has been described with regards to the preferred embodiment, it is recognized that alternative embodiment may be devised which would not depart from the present invention.

What I claim is:

1. An insertion device for inserting an implant into a spine during spinal surgery, said insertion device comprising:
a first member having means for engaging the implant to prevent the implant from moving axially apart from axial movement of said first member; and
a second member having means for engaging the implant to prevent the implant from rotating separate from said second member, said first and second members cooperating to lockably engage the implant such that during insertion of the implant said insertion device can be rotated in either direction, pushed, and pulled by said second member without disengaging the implant from said second member of said insertion device.

2. The insertion device of claim 1, wherein said engaging means of said first member includes a threaded portion.

3. The insertion device of claim 1, wherein said engaging means of said second member includes a depression for receiving a complementing raised portion of the implant.

4. The insertion device of claim 1, wherein the implant has a first cooperating member and said engaging means of said second member comprises a corresponding second cooperating member for cooperatively engaging said first cooperating member.

5. The insertion device of claim 1, further comprising a handle attached to said second member for providing leverage during rotation in either direction, pushing, and pulling of the insertion device.

6. A system for inserting into a spine during spinal surgery an interbody spinal implant, an instrument of said system comprising:
a first portion configured to engage the implant and to impart axial movement to the implant; and
a second portion configured to engage the implant to rotate the implant, said first and second portions cooperating to lockably engage the implant such that during insertion of the implant said instrument can be rotated in either direction, pushed, and pulled by said second portion without disengaging the implant from said second portion of said instrument.

7. The system of claim 6, wherein said first portion includes a thread.

8. The system of claim 6, wherein said second portion includes a depression for receiving a complementary raised portion of the implant.

9. The system of claim 6, wherein the implant has a first cooperating member and said second portion comprises a corresponding second cooperating member for cooperatively engaging the first cooperating member of the implant.

10. The system of claim 6, further comprises a handle attached to said second portion for exerting force during rotation in either direction, pushing, and pulling of the instrument.

11. The system of claim 6, further comprising an implant for promoting fusion between adjacent vertebral bodies, said implant having upper and lower surfaces for placement between and in contact with the adjacent vertebral bodies, each of said upper and lower surfaces having at least one opening adapted to permit bone from the adjacent vertebral bodies to grow through said implant.

12. The system of claim 11, further comprising a hollow between said upper and lower surfaces for holding bone growth promoting material.

13. The system of claim 12, wherein said at least one opening of each of said upper and lower surfaces are in communication with said hollow to permit bone from adjacent vertebral bodies to grow through said implant.

14. The system of claim 11, wherein said implant is made of an implant material other than bone.

15. The system of claim 11, wherein said implant is formed of a material stronger than the adjacent vertebral bodies in contact with said implant.

16. A surgical instrument for inserting a spinal implant into a human spine, said instrument comprising;
a shaft having a proximal end, a distal end opposite said proximal end, and a mid-longitudinal axis through said proximal and distal ends, said distal end having a projection extending therefrom adapted to engage a trailing end of the implant, said projection having a maximum dimension in a plane transverse to the mid-longitudinal axis of said shaft, said distal end having a stepped portion forming an engagement wall extending in a plane parallel to the mid-longitudinal axis of said shaft, said engagement wall being configured to contact an engagement surface on the implant, said engagement wall having a maximum dimension transverse to the mid-longitudinal axis of said shaft that is greater than the maximum transverse dimension of said projection.

17. The instrument of claim 16, further comprising at least a second engagement wall extending in a plane parallel to the mid-longitudinal axis of said shaft.

18. The instrument of claim 17, wherein said engagement walls are parallel to one another.

19. The instrument of claim 17, wherein said engagement walls define a recess therebetween.

20. The instrument of claim 19, wherein said recess has a minimum dimension transverse to the mid-longitudinal axis of said shaft that is greater than the maximum transverse dimension of said projection.

21. The instrument of claim 17, wherein said engagement walls face each other.

22. The instrument of claim 16, wherein said engagement wall extends to an outer perimeter of said distal end.

23. The instrument of claim 16, wherein said engagement wall extends to an outer perimeter at more than one location along the outer perimeter.

24. The instrument of claim 16, wherein said engagement wall includes a portion that is linear.

25. The instrument of claim 16, wherein said engagement wall has a maximum length transverse to the mid-longitudinal axis of said shaft, said engagement wall being linear along its entire length.

26. The instrument of claim 16, wherein said shaft has a maximum dimension transverse to the mid-longitudinal axis of said shaft, said engagement wall having a maximum length transverse to the mid-longitudinal axis of said shaft that is less than the maximum transverse dimension of said shaft.

27. The instrument of claim 16, wherein said engagement wall has a maximum height parallel to the mid-longitudinal axis of said shaft, said projection extending beyond the maximum height of said engagement wall.

28. The instrument of claim 16, wherein said projection is moveable relative to said engagement wall.

29. The instrument of claim 16, wherein said projection is coaxial with the mid-longitudinal axis of said shaft.

30. The instrument of claim 16, wherein said shaft includes a passage from said proximal end to said distal end.

31. The instrument of claim 30, wherein said projection is a distal end of a rod insertable in said passage.

32. The instrument of claim 16, wherein said projection is adapted to rotationally engage the trailing end of the implant.

33. The instrument of claim 16, wherein said projection includes a thread.

34. The instrument of claim 16, wherein said projection is substantially limited to rotational and axial movement.

35. The instrument of claim 16, wherein said projection has a cross section transverse to the mid-longitudinal axis of said shaft that is circular.

36. The instrument of claim 16, wherein said shaft has a maximum dimension transverse to the mid-longitudinal axis of said shaft that is more than twice the transverse maximum dimension of said projection.

37. The instrument of claim 16, wherein said shaft has a maximum dimension transverse to the mid-longitudinal axis of said shaft that is more than three times the transverse maximum dimension of said projection.

38. The instrument of claim 30, wherein said shaft has a length and said passage has a variable cross section transverse to the mid-longitudinal axis of said shaft along at least a portion of the length of said shaft.

39. The instrument of claim 30, wherein said projection is moveable relative to said shaft, said passage including a depth stop adapted to limit axial movement of said projection into the implant.

40. The instrument of claim 39, wherein said depth stop includes a shoulder.

41. The instrument of claim 16, wherein said shaft has a cross section transverse to the mid-longitudinal axis of said shaft that becomes larger proximate said distal end of said shaft.

42. The instrument of claim 16, wherein said shaft has a cross section transverse to the mid-longitudinal axis of said shaft proximate said distal end that is adapted to substantially match an outer cross section of the trailing end of the implant.

43. The instrument of claim 16, wherein said distal end includes a planar portion transverse to the mid-longitudinal axis of said shaft.

44. The instrument of claim 16, further comprising a handle adapted to move said projection into engagement with the implant.

45. The instrument of claim 44, wherein said handle is knurled.

46. The instrument of claim 16, wherein said shaft further comprises a handle.

47. The instrument of claim 46, wherein said handle extends transverse to the mid-longitudinal axis of said shaft.

48. The instrument of claim 46, wherein said handle forms a T-shape with said shaft.

49. A surgical instrument for inserting a spinal implant through a hollow sleeve and into a human spine, said instrument comprising;
- a shaft adapted to be inserted into the hollow sleeve, said shaft having a proximal end, a distal end opposite said proximal end, a length from said proximal end to said distal end, and a mid-longitudinal axis through said proximal and distal ends, said shaft having a passage from said proximal end to said distal end, said shaft having a depth stop configured to limit insertion of said shaft into the hollow sleeve, said shaft having an outer wall that is parallel to the mid-longitudinal axis along at least a portion of the length of said shaft; and
- a rod insertable into said passage of said shaft, said rod having a proximal end and a distal end, said distal end of said rod being configured to engage the implant, said rod when engaged within said shaft having a depth stop limiting axial movement of said shaft within said passage, said depth stop of said rod being a distance from the distal end of said shaft, said depth stop of said shaft being a distance from the distal end of said shaft, the distance of said rod being less than the distance of said shaft.

50. The instrument of claim 49, wherein said distal end of said shaft has a stepped portion forming an engagement wall extending in a plane parallel to the mid-longitudinal axis of said shaft, said engagement wall being configured to contact an engagement surface on the implant.

51. The instrument of claim 50, further comprising at least a second engagement wall extending in a plane parallel to the mid-longitudinal axis of said shaft.

52. The instrument of claim 51, wherein said engagement walls are parallel to one another.

53. The instrument of claim 51, wherein said engagement walls define a recess therebetween.

54. The instrument of claim 53, wherein said recess has a minimum dimension transverse to the mid-longitudinal axis of said shaft that is greater than the maximum transverse dimension of said rod.

55. The instrument of claim 51, wherein said engagement walls face each other.

56. The instrument of claim 50, wherein said engagement wall extends to an outer perimeter of said distal end.

57. The instrument of claim 50, wherein said engagement wall extends to an outer perimeter at more than one location along the outer perimeter.

58. The instrument of claim 50, wherein said engagement wall includes a portion that is linear.

59. The instrument of claim 50, wherein said engagement wall has a maximum length transverse to the mid-longitudinal axis of said shaft, said engagement wall being linear along its entire length.

60. The instrument of claim 50, wherein said shaft has a maximum dimension transverse to the mid-longitudinal axis of said shaft, said engagement wall having a maximum length transverse to the mid-longitudinal axis of said shaft that is less than the maximum transverse dimension of said shaft.

61. The instrument of claim 50, wherein said engagement wall has a maximum height parallel to the mid-longitudinal axis of said shaft, said rod extending beyond the maximum height of said engagement wall.

62. The instrument of claim 50, wherein said rod is moveable relative to said engagement wall.

63. The instrument of claim 49, wherein said rod is coaxial with the mid-longitudinal axis of said shaft.

64. The instrument of claim 49, wherein said rod is adapted to rotationally engage the trailing end of the implant.

65. The instrument of claim 49, wherein said rod includes a thread.

66. The instrument of claim 49, wherein said rod is substantially limited to rotational and axial movement.

67. The instrument of claim 49, wherein said rod has a cross section transverse to the mid-longitudinal axis of said shaft that is circular.

68. The instrument of claim 49, wherein said shaft has a maximum dimension transverse to the mid-longitudinal axis of said shaft that is more than twice the transverse maximum dimension of said rod.

69. The instrument of claim 49, wherein said shaft has a maximum dimension transverse to the mid-longitudinal axis of said shaft that is more than three times the transverse maximum dimension of said rod.

70. The instrument of claim 49, wherein said shaft has a cross section transverse to the mid-longitudinal axis of said shaft proximate said distal end that is adapted to substantially match an outer cross section of a trailing end of the implant.

71. The instrument of claim 49, further comprising a handle adapted to move said rod into engagement with the implant.

72. The instrument of claim 71, wherein said handle is knurled.

73. The instrument of claim 49, wherein said shaft further comprises a handle.

74. The instrument of claim 73, wherein said handle extends transverse to the mid-longitudinal axis of said shaft.

75. The instrument of claim 73, wherein said handle forms a T-shape with said shaft.

76. A surgical instrument for inserting a spinal implant into a human spine, said instrument comprising;
- a shaft having a proximal end, a distal end opposite said proximal end, and a mid-longitudinal axis through said proximal and distal ends, said distal end having a projection extending therefrom adapted to engage a trailing end of the implant, said distal end having a stepped portion forming an engagement wall extending in a plane parallel to the mid-longitudinal axis of said shaft, said engagement wall being configured to contact an engagement surface on the implant, said distal end of said shaft having a maximum width transverse to the mid-longitudinal axis of said shaft, said engagement wall having a dimension in the plane parallel to the mid-longitudinal axis of said shaft that extends across a majority of the width of said distal end of said shaft.

77. The instrument of claim 76, further comprising at least a second engagement wall extending in a plane parallel to the mid-longitudinal axis of said shaft.

78. The instrument of claim 77, wherein said engagement walls are parallel to one another.

79. The instrument of claim 77, wherein said engagement walls define a recess therebetween.

80. The instrument of claim 79, wherein said recess has a minimum dimension transverse to the mid-longitudinal axis of said shaft that is greater than the maximum transverse dimension of said projection.

81. The instrument of claim 77, wherein said engagement walls face each other.

82. The instrument of claim 76, wherein said engagement wall extends to an outer perimeter of said distal end.

83. The instrument of claim 76, wherein said engagement wall extends to an outer perimeter at more than one location along the outer perimeter.

84. The instrument of claim 76, wherein said engagement wall includes a portion that is linear.

85. The instrument of claim 76, wherein said engagement wall has a maximum length transverse to the mid-longitudinal axis of said shaft, said engagement wall being linear along its entire length.

86. The instrument of claim 76, wherein said shaft has a maximum dimension transverse to the mid-longitudinal axis of said shaft, said engagement wall having a maximum length transverse to the mid-longitudinal axis of said shaft that is less than the maximum transverse dimension of said shaft.

87. The instrument of claim 76, wherein said engagement wall has a maximum height parallel to the mid-longitudinal axis of said shaft, said projection extending beyond the maximum height of said engagement wall.

88. The instrument of claim 76, wherein said projection is moveable relative to said engagement wall.

89. The instrument of claim 76, wherein said projection is coaxial with the mid-longitudinal axis of said shaft.

90. The instrument of claim 76, wherein said shaft includes a passage from said proximal end to said distal end.

91. The instrument of claim 90, wherein said projection is a distal end of a rod insertable in said passage.

92. The instrument of claim 76, wherein said projection is adapted to rotationally engage the trailing end of the implant.

93. The instrument of claim 76, wherein said projection includes a thread.

94. The instrument of claim 76, wherein said projection is substantially limited to rotational and axial movement.

95. The instrument of claim 76, wherein said projection has a cross section transverse to the mid-longitudinal axis of said shaft that is circular.

96. The instrument of claim 76, wherein said shaft has a maximum dimension transverse to the mid-longitudinal axis of said shaft that is more than twice the transverse maximum dimension of said projection.

97. The instrument of claim 76, wherein said shaft has a maximum dimension transverse to the mid-longitudinal axis of said shaft that is more than three times the transverse maximum dimension of said projection.

98. The instrument of claim 90, wherein said projection is moveable relative to said shaft, said passage including a depth stop adapted to limit axial movement of said projection into the implant.

99. The instrument of claim 98, wherein said depth stop includes a shoulder.

100. The instrument of claim 76, wherein said shaft has a cross section transverse to the mid-longitudinal axis of said shaft that becomes larger proximate said distal end of said shaft.

101. The instrument of claim 76, wherein said shaft has a cross section transverse to the mid-longitudinal axis of said shaft proximate said distal end that is adapted to substantially match an outer cross section of the trailing end of the implant.

102. The instrument of claim 76, wherein said distal end includes a planar portion transverse to the mid-longitudinal axis of said shaft.

103. The instrument of claim 76, further comprising a handle adapted to move said projection into engagement with the implant.

104. The instrument of claim 103, wherein said handle is knurled.

105. The instrument of claim 76, wherein said shaft further comprises a handle.

106. The instrument of claim 105, wherein said handle extends transverse to the mid-longitudinal axis of said shaft.

107. The instrument of claim 105, wherein said handle forms a T-shape with said shaft.

108. A surgical instrument for inserting a spinal implant into a human spine, said instrument comprising:
a shaft having a proximal end, a distal end opposite said proximal end, a length from said proximal end to said distal end, and a mid-longitudinal axis through said proximal and distal ends, said shaft including a passage from said proximal end to said distal end, said distal end including a planar portion transverse to the mid-longitudinal axis of said shaft, said planar portion being adapted to interdigitate with a trailing end of the implant; and
a rod adapted to rotate within said passage of said shaft, said rod having a proximal end, a distal end configured to engage the implant, and a length from said proximal end to said distal end, the length of said shaft being greater than one-half the length of said rod.

109. The instrument of claim 108, wherein said distal end of said shaft has a stepped portion forming an engagement wall extending in a plane parallel to the mid-longitudinal axis of said shaft, said engagement wall being configured to contact an engagement surface on the implant.

110. The instrument of claim 109, further comprising at least a second engagement wall extending in a plane parallel to the mid-longitudinal axis of said shaft.

111. The instrument of claim 110, wherein said engagement walls are parallel to one another.

112. The instrument of claim 110, wherein said engagement walls define a recess therebetween.

113. The instrument of claim 112, wherein said recess has a minimum dimension transverse to the mid-longitudinal axis of said shaft that is greater than the maximum transverse dimension of said rod.

114. The instrument of claim 110, wherein said engagement walls face each other.

115. The instrument of claim 109, wherein said engagement wall extends to an outer perimeter of said distal end.

116. The instrument of claim 109, wherein said engagement wall extends to an outer perimeter at more than one location along the outer perimeter.

117. The instrument of claim 109, wherein said engagement wall includes a portion that is linear.

118. The instrument of claim 109, wherein said engagement wall has a maximum length transverse to the mid-longitudinal axis of said shaft, said engagement wall being linear along its entire length.

119. The instrument of claim 109, wherein said shaft has a maximum dimension transverse to the mid-longitudinal axis of said shaft, said engagement wall having a maximum length transverse to the mid-longitudinal axis of said shaft that is less than the maximum transverse dimension of said shaft.

120. The instrument of claim 109, wherein said engagement wall has a maximum height parallel to the mid-longitudinal axis of said shaft, said rod extending beyond the maximum height of said engagement wall.

121. The instrument of claim 109, wherein said rod is moveable relative to said engagement wall.

122. The instrument of claim 108, wherein said rod is coaxial with the mid-longitudinal axis of said shaft.

123. The instrument of claim 108, wherein said rod is adapted to rotationally engage the trailing end of the implant.

124. The instrument of claim 108, wherein said rod includes a thread.

125. The instrument of claim 108, wherein said rod is substantially limited to rotational and axial movement.

126. The instrument of claim 108, wherein said rod has a cross section transverse to the mid-longitudinal axis of said shaft that is circular.

127. The instrument of claim 108, wherein said shaft has a maximum dimension transverse to the mid-longitudinal axis of said shaft that is more than twice the transverse maximum dimension of said rod.

128. The instrument of claim 108, wherein said shaft has a maximum dimension transverse to the mid-longitudinal axis of said shaft that is more than three times the transverse maximum dimension of said rod.

129. The instrument of claim 108, wherein said shaft has a cross section transverse to the mid-longitudinal axis of said shaft proximate said distal end that is adapted to substantially match an outer cross section of a trailing end of the implant.

130. The instrument of claim 108, further comprising a handle adapted to move said rod into engagement with the implant.

131. The instrument of claim 130, wherein said handle is knurled.

132. The instrument of claim 108, wherein said shaft further comprises a handle.

133. The instrument of claim 132, wherein said handle extends transverse to the mid-longitudinal axis of said shaft.

134. The instrument of claim 132, wherein said handle forms a T-shape with said shaft.

* * * * *

UNITED STATES PATENT AND TRADEMARK OFFICE
CERTIFICATE OF CORRECTION

PATENT NO. : 7,452,359 B1
APPLICATION NO. : 08/480684
DATED : November 18, 2008
INVENTOR(S) : Gary Karlin Michelson It is certified that error appears in the above-identified patent and that said Letters Patent is hereby corrected as shown below:

Title Page, Item (56)
Page 3, Column 2, Foreign Patent Documents:
Line 1: delete "SE  108 101  7/1939"; and
Line 5: delete "SU  1217374  3/1985".

Title Page, Item (56)
Page 3, Column 2, Other Publications:
Line 31: after "Related" insert -- Research --;
Line 50: change "Coller" to -- Cotler --;
Line 52: change "1998" to -- 1996 --;
Line 53: change "in th" to -- in the --; and
Line 56: change "Fatal H ad" to -- Fatal Head --; and change "123-31" to -- 23-31 --.

Title Page, Item (56)
Page 4, Column 1, Other Publications:
Line 6: change "Meningloma" to -- Meningloma --;
Line 14: change "Rekonstruktionsmoglichkelten" to -- Rekonstruktionsmoglichkeiten --;
Line 15: change "knochemen" to -- knochernen --;
Line 22: change "Assocation" to -- Association --;
Line 31: change "281-284" to -- 281-294 --;
Line 35: change "dern" to -- dem --;
Line 43: change "Arthr desis" to -- Arthrodesis --; and
Line 44: change "Metacarpophelengeal" to -- Metacarpophalangeal --.

UNITED STATES PATENT AND TRADEMARK OFFICE
CERTIFICATE OF CORRECTION

PATENT NO.         : 7,452,359 B1
APPLICATION NO. : 08/480684
DATED              : November 18, 2008
INVENTOR(S)        : Gary Karlin Michelson It is certified that error appears in the above-identified patent and that said Letters Patent is hereby corrected as shown below:

Title Page, Item (56)
<u>Page 4, Column 2, Other Publications</u>:
Line 16: change "Verterbral" to -- Vertebral --; and
Line 29: change "Scietific" to -- Scientific --.

Signed and Sealed this

Twentieth Day of January, 2009

JON W. DUDAS
*Director of the United States Patent and Trademark Office*